US00PP14020P39

(12) United States Plant Patent
Watson

(10) Patent No.: US PP14,020 P3
(45) Date of Patent: Jul. 29, 2003

(54) PLUM TREE NAMED 'KENMORE PLUM'

(75) Inventor: John P. Watson, deceased, late of Phelps, NY (US), by Judith Watson, executrix

(73) Assignee: Cornell Research Foundation, Inc., Ithaca, NY (US)

( * ) Notice: Subject to any disclaimer, the term of this patent is extended or adjusted under 35 U.S.C. 154(b) by 4 days.

(21) Appl. No.: 09/894,309

(22) Filed: Jun. 26, 2001

(65) Prior Publication Data

US 2003/0005497 P1 Jan. 2, 2003

(51) Int. Cl.[7] ..... A01H 5/00

(52) U.S. Cl. ..... Plt./185

(58) Field of Search ..... Plt./185, 184

*Primary Examiner*—Bruce R. Campell
*Assistant Examiner*—June Hwu

(57) ABSTRACT

A new a distinct variety of prune plum tree, *Prunus domestica,* originating as a hybrid seedling of the cross: 'Standard'(non-patented)×'Stanley'(non-patented). This new variety is unique from its parents and other prune plums because it is has a freestone, non-shattering stone and flesh which processes very well yielding highly colored, high quality plum products. It is also more vigorous and pest tolerant than other commercial prune plum varieties grown at this time.

9 Drawing Sheets

*Prunus domestica*'Kenmore Plum'.

FIELD OF THE INVENTION

A new and distinct variety of European-type plum tree originated as a seedling of *Prunus domestica* in the breeding program of Cornell University and is hereinafter referred to as 'Kenmore Plum'. This new variety is unique because the fruit has several traits that make it favorable for processing uses (high quality, free stone, non-shattering stone, high color retention of processed fruit products) and the tree is more vigorous and more pest tolerant than other current commercial varieties of European plums with which it has been compared.

SUMMARY OF THE INVENTION

This new and distinct variety of European plum was discovered in 1971 by John P. Watson (deceased), a plant breeder at the New York State Agricultural Experiment Station, Geneva, N.Y., a research unit of Cornell University, hereinafter referred to as Geneva Experiment Station. By breeding methodology convention at the Geneva Experiment Station it was designated as NY 58.900.9 because it belonged to the Geneva Experiment Station Breeding Record Number 58.900, a hybrid population of trees that resulted from hybridizing the varieties 'Standard' (non-patented)×'Stanley'(non-patented), and this seedling was the ninth seedling chosen for further evaluation from in a population of 295 siblings possessing the same parentage. The orchard location where the seedling was grown and first noticed was designated as Crittenden Farm Field Number 30, Row 9, Tree 263. This seedling was first noticed because it had fruit that was similar to its parent, 'Stanley'(non-patented), in many traits, but was superior to 'Stanley'(non-patented) in freeness of the stone. In 1971, buds were taken from the original tree and trees for further testing were asexually reproduced by T-budding and chip budding techniques. This new cultivar has been reproduced on plum, *Prunus domestica,* and peach seedling, *Prunus persica,* rootstocks by Hilltop Nursery LLC, Hartford, Mich. and remains true to the description herein contained.

BRIEF DESCRIPTION OF THE DRAWINGS

The accompanying photographs show typical specimens of the new variety as depicted in color as nearly true as is reasonably possible in color illustrations of this character. These specimens were obtained at the Geneva Experiment Station, Geneva, N.Y.

BOTANICAL DESCRIPTION OF THE PLANT

Figure 1:
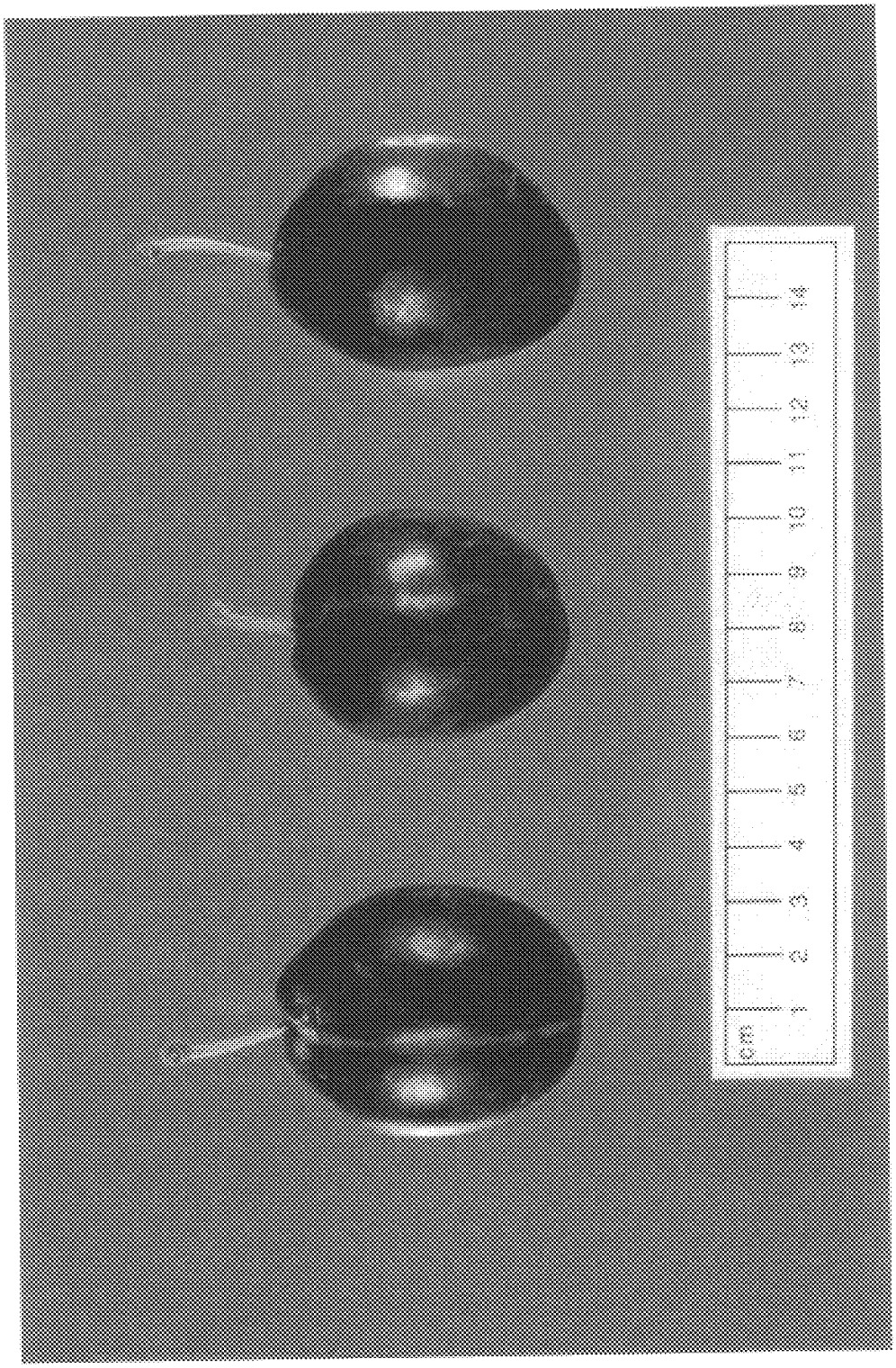
FIG. 1. illustrates the intact fruit of the new variety at maturity.
Figure 2:
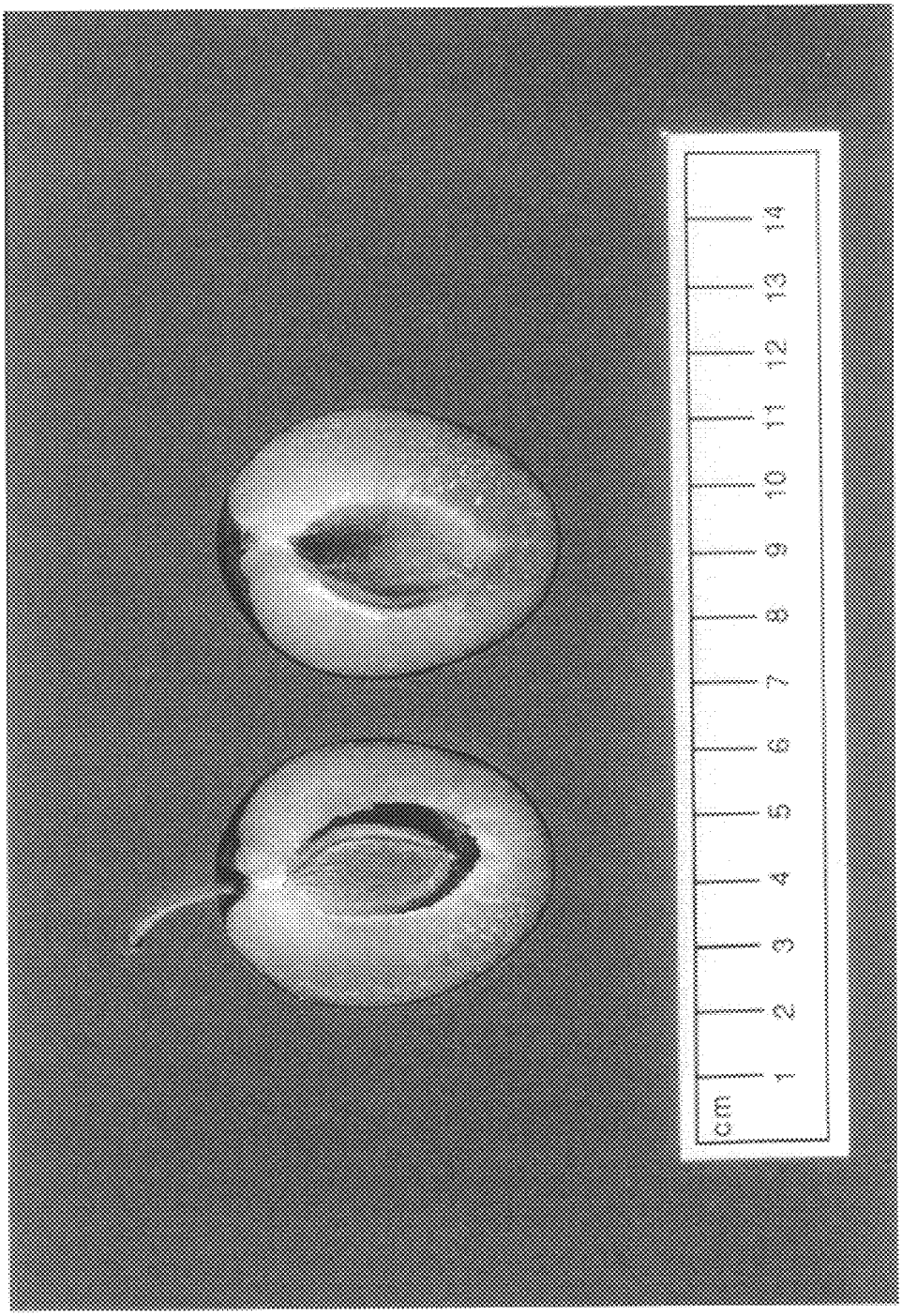
FIG. 2. illustrates the fruit halves of the new variety as cut at the suture line.
Figure 3:
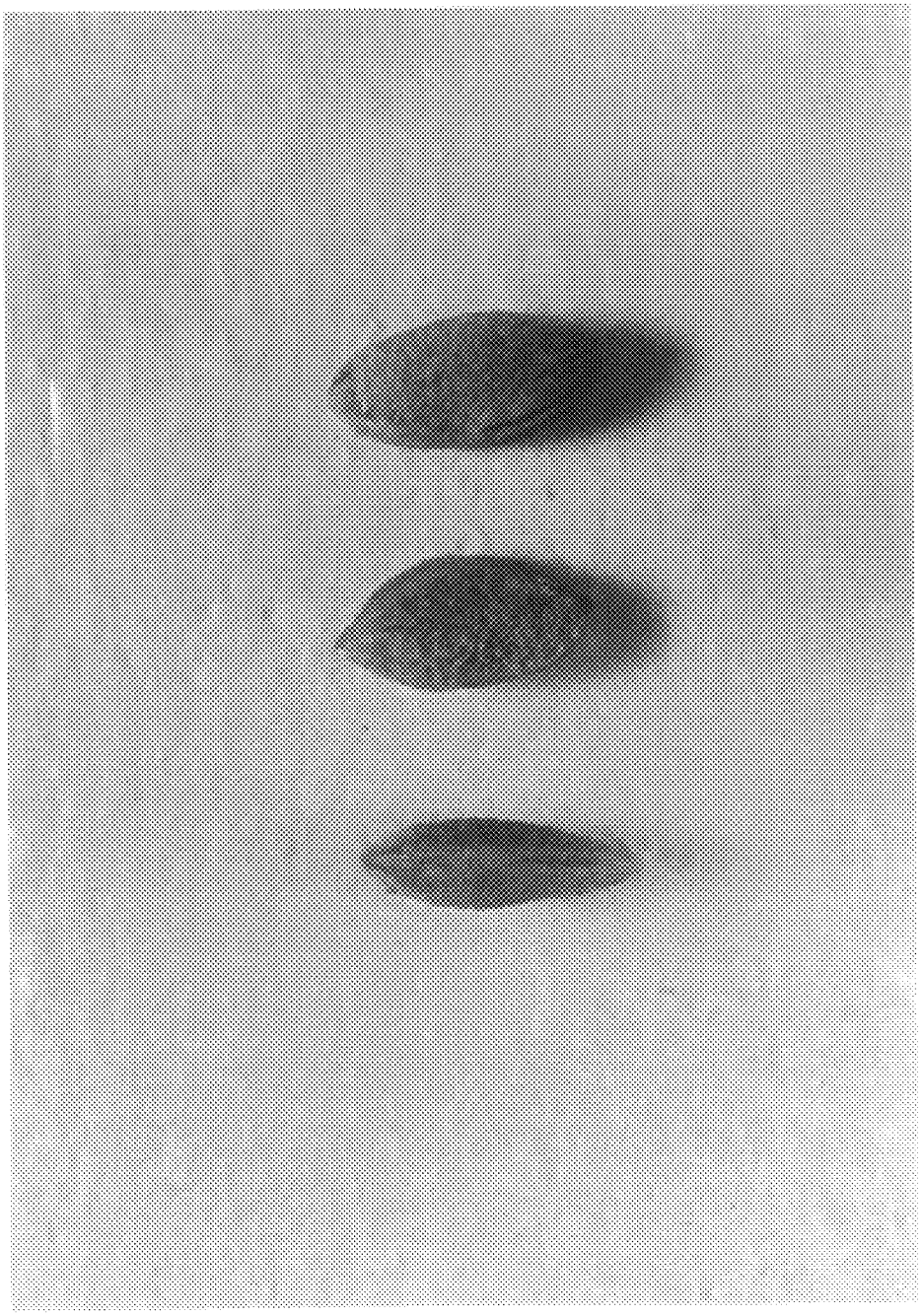
FIG. 3. illustrates the stone of the new variety as extracted from the mature fruit.
Figure 4:
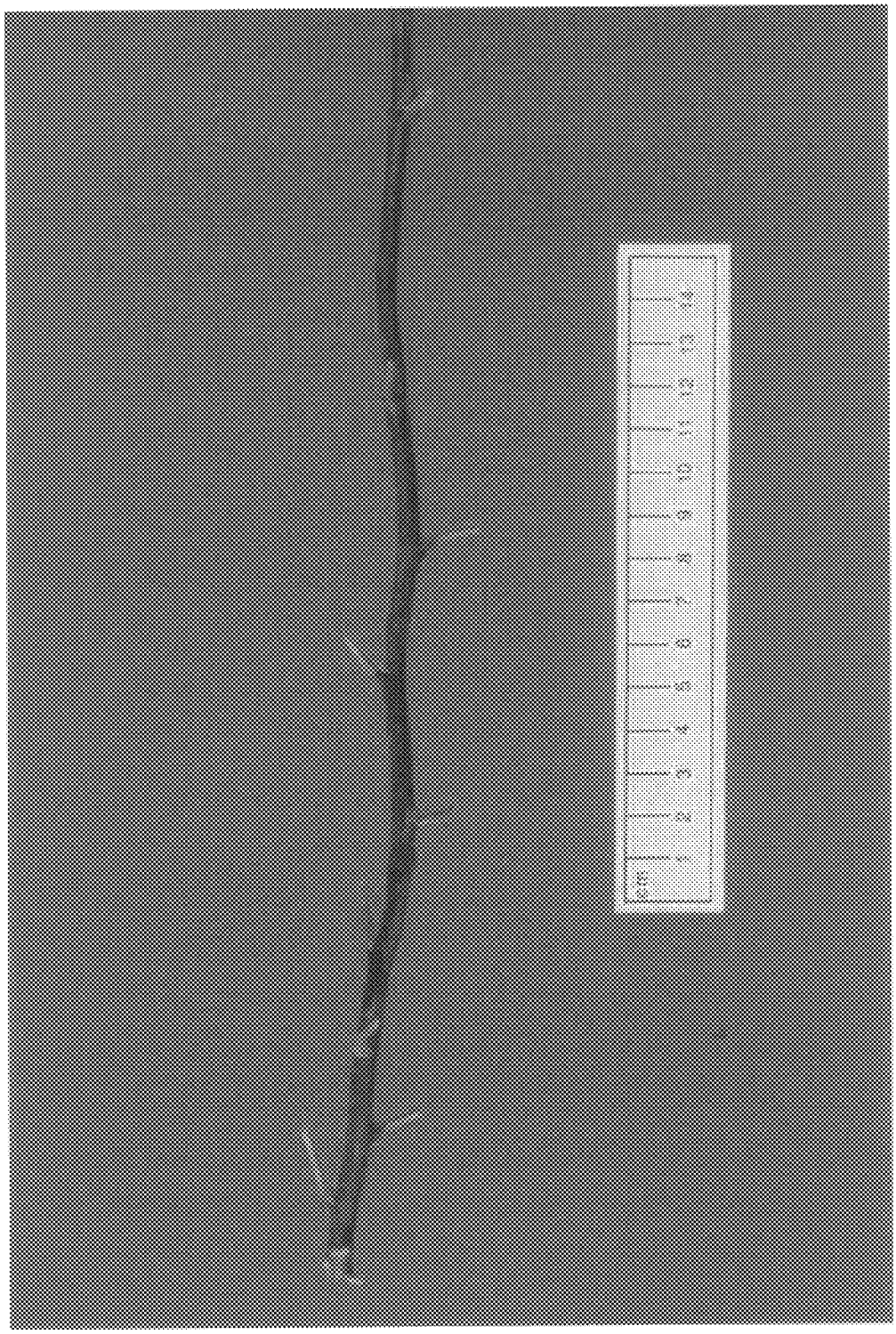
FIG. 4. illustrates a vegetative twig of the new variety from the annual, apical growth of a lateral branch in the year 2000.
Figure 5:
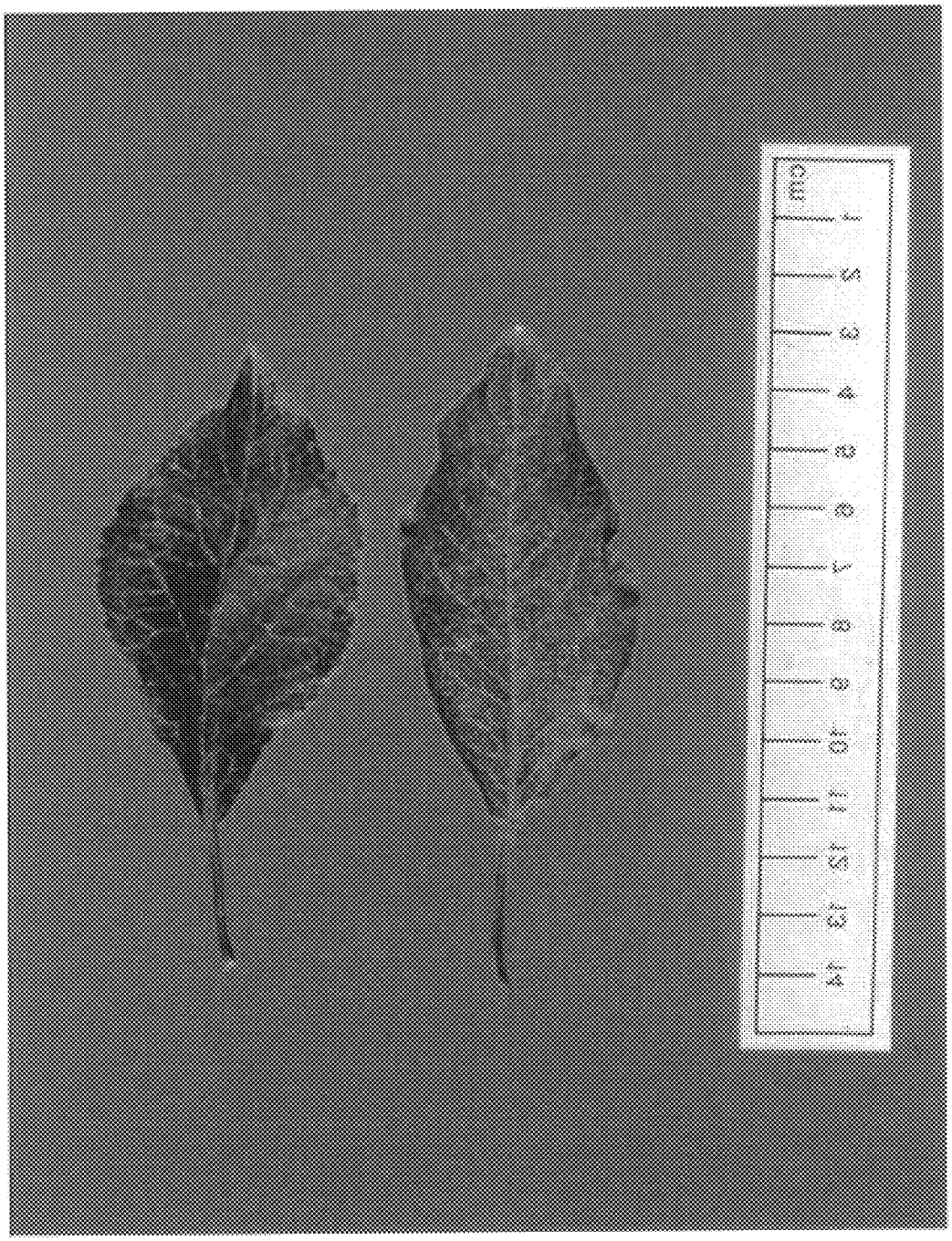
FIG. 5. illustrates the adaxial surface of two leaves of the new variety taken from the vegetative twig shown in FIG. 4.
Figure 6:
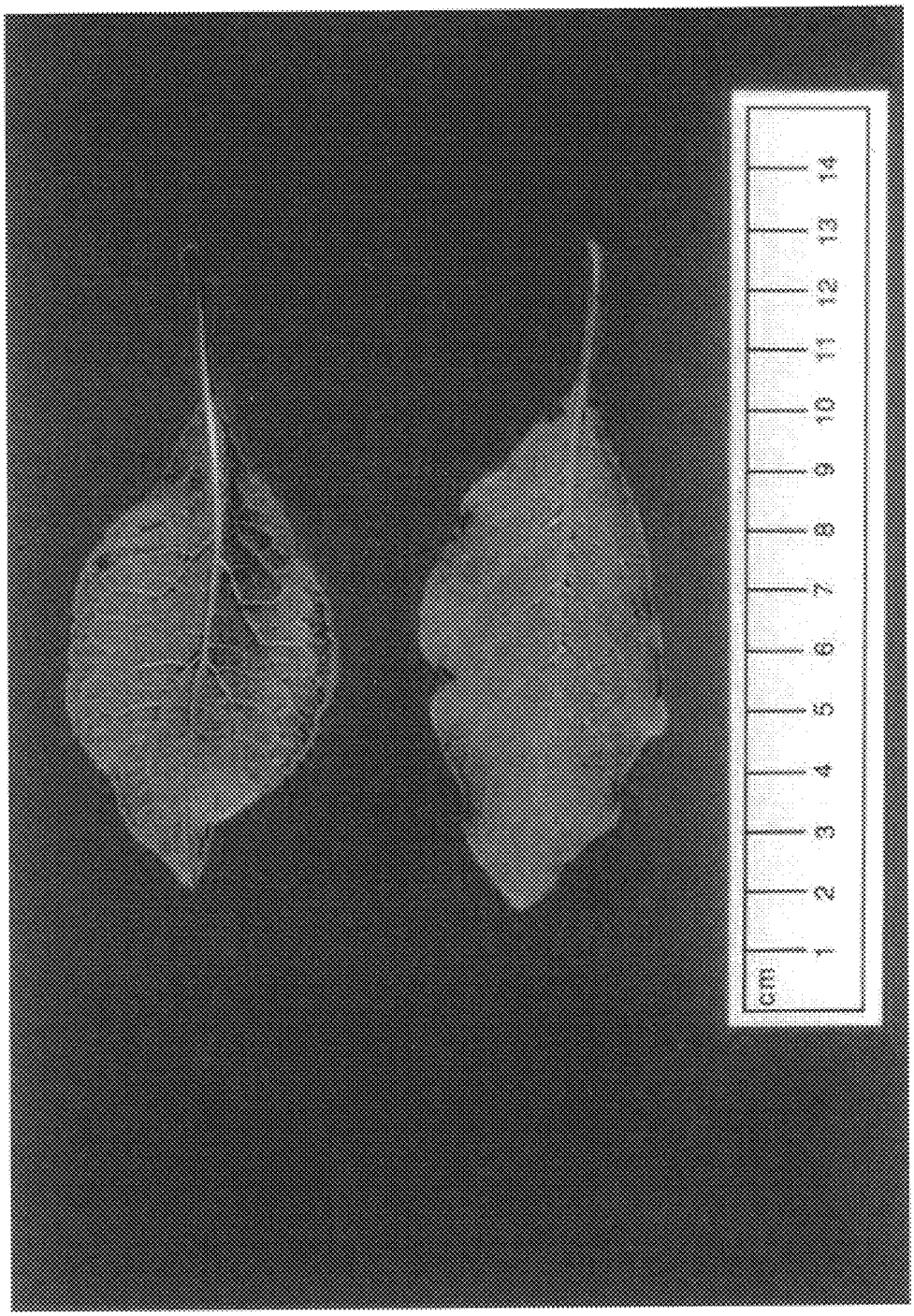
FIG. 6. illustrates the abaxial surface of two leaves shown in FIG. 5.
Figure 7:
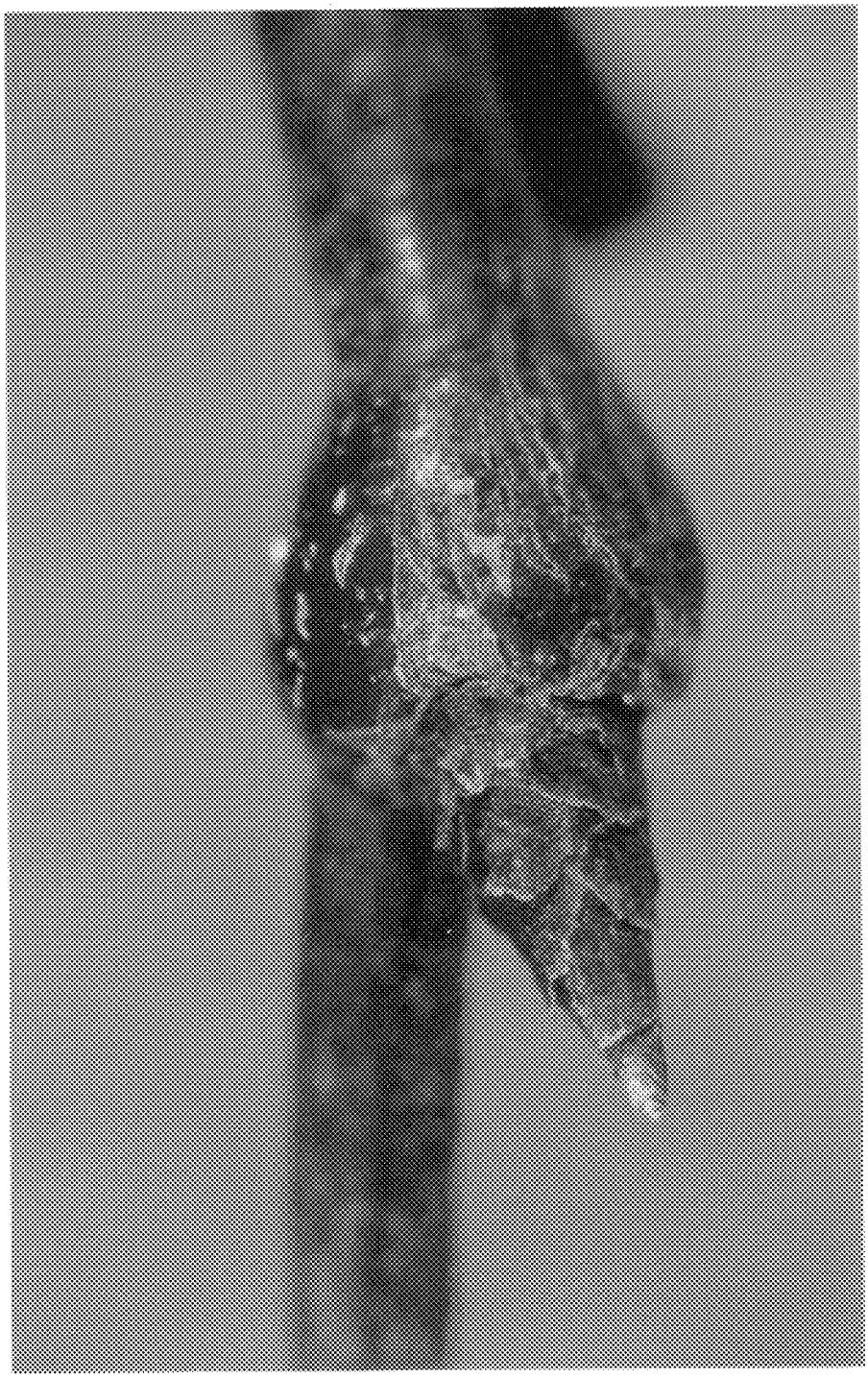
FIG. 7. illustrates vegetative buds of the new variety in close-up.
Figure 8:
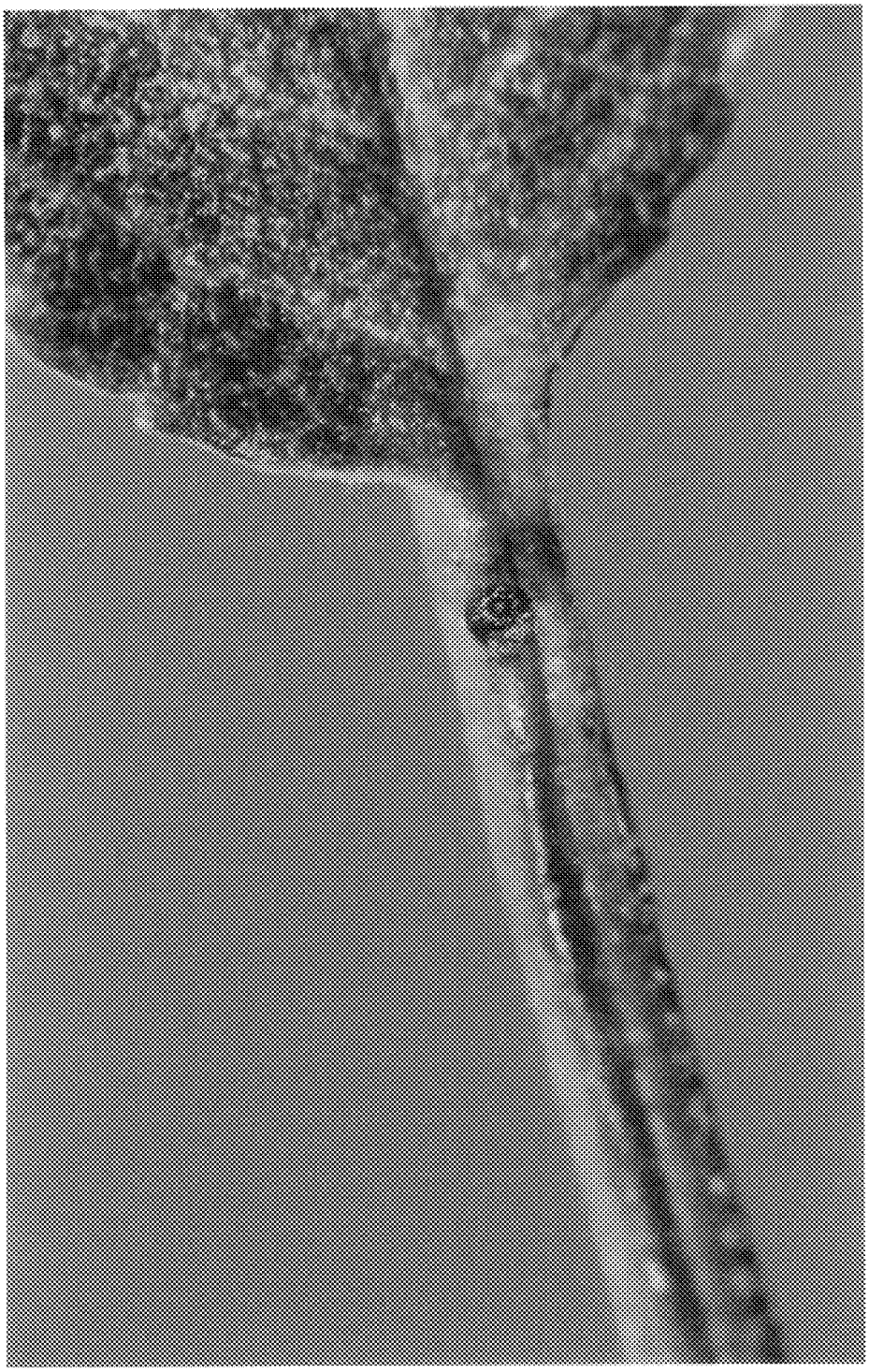
FIG. 8. illustrates a close-up view of leaf petiole and gland at base of leaf blade.
Figure 9:
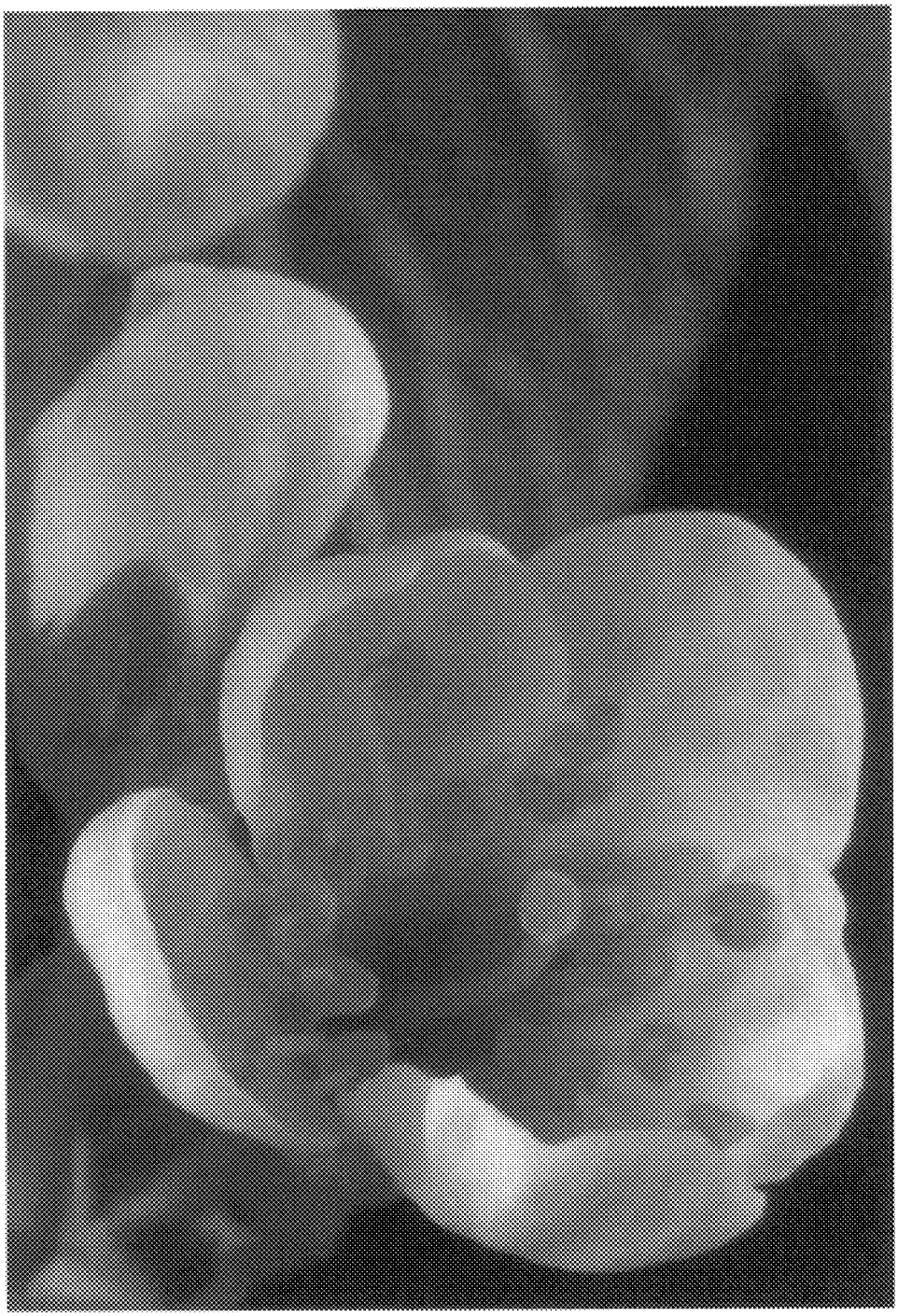
FIG. 9. illustrates the blossoms of the new variety.

A detailed description of the cultivar Kenmore Plum cultivar follows using The Royal Horticultural Society of London Colour Chart for color identification except where general color terms are sufficient.

Parentage: A hybrid seedling of the cross: 'Standard'(non-patented)×'Stanley'(non-patented). Locality of the original discovery and observations is the Crittenden Farm Research Orchard Number 30, Row 9, tree 263, Geneva Experiment Station, Geneva, N.Y., U.S.A.

Tree:

*Age of specimen.*—42 years old.

*Height.*—4 M.

*Width.*—3.5 M.

*Size.*—Medium large.

*Vigor.*—Medium high.

*Density.*—Medium.

*Form.*—Upright, with medium level of lateral branching.

*Production*—Heavy at full maturity, but slow to achieve mature yield capacity if grown in vigorous level of cultural management.

*Bearing.*—Annual on spurs and one year old shoots.

*Disease resistance.*—More tolerant to black knot fungus of the wood than 'Stanley'(non-patented); similar to 'Stanley'(non-patented) in tolerance level to brown rot of the blossoms and fruit; immune to Prune Leafcasting Mottle which is a serious physiological disorder of the 'Italian Prune' and most of its progeny.

*Insect resistance.*—More tolerant to attack of European red mite than 'Stanley'(non-patented) and 'Jayfree Plum'(patent application Ser. No. 09/894,312).

*Cold hardiness.*—Good, crops regularly in test orchards in commercial fruit districts of New York and Michigan.

*Graft compatibility.*—Good, produces compatible graft unions with 'Mariana 2624', 'GF 8-1 Mariana', Myrobolan Seedling and Peach Seedling rootstocks.

Trunk:

*Size.*—37 cm in diameter at 60 cm above ground level.

*Surface.*—New bark is smooth with prominent lenticels, older bark is rough.

*Lenticels.*—Sparse in number, varying in length from 2 to 3.5 mm and width from 0.75 to 1.0 mm, prominent, horizontal, elliptical, White 155 D.

*Older bark.*—Grey Group 201 D where directly exposed to the sun and Grey Group 201 A where less exposed to sunlight.

*Newer bark.*—Brown Group 200 D.

Vegetative buds:

*Placement.*—At the arch of irregular, wavy pattern of wood growth.

*Appearance.*—Pointed and surrounding bark is non-pubescent.

*Length.*—4.5 mm.

*Width.*—3 mm at base.

*Color.*—Grayed Purple Group 183D to Black 202B.

*Internode length.*—4 cm.

*Spur.*—Pointed apical buds at tips of spurs.

Leaves:

*Size.*—8.0 to 8.5 cm in length, to 4.0 cm in width.

*Form.*—Elliptic.

*Thickness.*—Medium.

*Margin.*—Serrated with variable shapes with rounded with regularly spaced alternating deep and shallow notches.

*Adaxial surface.*—Smooth, but not shiny green, Green Group 136B.

*Abaxial surface.*—Dull luster to green coloration, Yellow Green Group 148B.

*Glands.*—None to few, small, round; color Yellow Green 148C.

*Anthocyanin coloration.*—59B, apparent on glands and upper ridges of petiole grooves.

*Stipules.*—None observed.

Petiole:

*Size.*—Length 2.75 to 3.25 cm, diameter 2 mm.

*Color.*—Green Group 136D with Red Purple Group 59B on ridges.

*Surface texture.*—Smooth, glossy with a prominent groove.

Flowers:

*Blooming period.*—Mid-late, May 3 to May 6 in Geneva, N.Y.

*Presentation.*—Non-showy.

*Fragrance.*—Faint, sweet.

*Fertility.*—Self-fertile.

*Pollen.*—Present, plentiful, good pollen source for 'Jayfree Plum' (patent application Ser. No. 09/894,312) selection.

*Corolla diameter.*—26 mm.

*Petals.*—Single, 5 in number, not overlapping, oval, length 12 mm, width 9 mm, margin very slightly wavy, soft texture, White 155 D.

*Number of flowers per cluster.*—2 to 5.

*Peduncle.*—1.9 to 2.2 cm. in length and 2 mm in width.

*Peduncle surface texture.*—Mildly pubescent.

*Peduncle color.*—Green Group 143C.

*Number of stamens.*—27 to 31.

*Filaments.*—Length 8 mm, width 0.3 mm, White 155 D.

*Anthers.*—Held above corolla, profuse pollen, Yellow 13 A.

*Style.*—Length 8 to 10 mm, color Yellow Orange Group 16B.

*Stigma.*—Round, diameter 5 mm, color Yellow Orange Group 17A.

*Sepals.*—5 in number, bluntly pointed at apex, Green 143 C.

Fruit:

*Maturity when described.*—Commercial ripeness, soluble solid content is 14 degrees Brix.

*Date of first picking.*—Late, mid-season ripening, September 8 at Geneva, N.Y.

*Size.*—5.2 to 6.0 cm in length, 4.0 to 4.5 cm in width.

*Form.*—Elongated, very slightly indented on stem end and pistallate end bluntly pointed.

*Base.*—Rounded with slight indentation at stem cavity.

*Stem cavity.*—Slight, under 1 mm.

*Stem scar.*—May develop cracks that extend into connecting suture tissues for up to 4 mm in length in high rainfall seasons.

*Apex.*—Bluntly pointed to rounded.

*Suture.*—Extends around dorsal surface, smooth, indented from 0.3 mm to 0.6 mm.

*Ventral surface.*—Smooth to very slightly indented at suture.

Skin:

*Thickness.*—Medium.

*Texture.*—Elastic, tough but not unpleasing.

*Tendency to crack.*—May split on suture adjacent to the stem scar/cavity in high rainfall seasons.

*Bloom.*—Present, but medium in its graying effect on skin color.

*Color.*—Grayed Purple Group 187A.

*Flavor.*—Fruity, sweet plum flavor with aromatic essence present.

Flesh:

*Texture.*—Medium firm, juicy, retains firm character of flesh after canning as halves.

*Acidity.*—Medium high until sugar level gets to above 12 degrees Brix.

*Flavor.*—Excellent with aromatic essence present.

*Aroma.*—Present, pleasing.

*Fibers.*—Few.

*Color.*—Grayed Yellow Group 162B with a background of Grayed Purple 185A.

*Coloration in the pit cavity.*—Same as flesh.

*Eating quality.*—Excellent when mature to 14 degrees Brix, slightly acid if eaten when immature.

Stone:

*Size.*—4.1 cm in length, 2.0 m in width at widest point near the center, 1.5 cm in width at widest point of the flatter direction.

*Form.*—Elliptical, asymmetrical, widest point at center.

*Apex.*—Pointed but not possessing a prominent tip.

*Sides.*—Very slightly winged on suture.

*Base.*—Pointed, possessing a similar shape to the apical end.

*Surface.*—Rough.

*Color.*—Grayed Orange 164A to Grayed Orange 164C.

*Type.*—Freestone at commercial maturity.

*Tendency to crack.*—Non-existent.

Stem:

*Length.*—16 mm, width 1.5 mm.

*Color.*—Green 138A.

*Texture.*—Very slightly pubescent.

Use: Dual purpose for either fresh market or processed as whole, halves, coarse puree' for bakery products, for infant food puree'.

I claim:

1. A new and distinct variety of European-type plum tree, *Prunus domestica,* substantially as herein shown and described, characterized as to novelty by the unique combination of a free, non-shattering stone, highly colored processed plum products of excellent quality, with above average tolerance for black knot disease of the wood, brown rot tolerance of the blossoms and fruit, and European red mite tolerance of the leaves, and possessing fresh market eating quality and shipping/handling attributes that meet grade standards for this fruit.

* * * * *